(12) United States Patent
Kern

(10) Patent No.: US 8,924,005 B2
(45) Date of Patent: Dec. 30, 2014

(54) METHOD AND SYSTEM FOR BIO-FLUID SAMPLING

(71) Applicant: University of Utah Research Foundation, Salt Lake City, UT (US)

(72) Inventor: Steven Edward Kern, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/656,266

(22) Filed: Oct. 19, 2012

(65) Prior Publication Data

US 2013/0123969 A1    May 16, 2013

Related U.S. Application Data

(60) Provisional application No. 61/551,001, filed on Oct. 25, 2011.

(51) Int. Cl.
*G06F 7/00* (2006.01)
*A61B 5/145* (2006.01)
*G05D 3/00* (2006.01)
*A61B 5/053* (2006.01)
*A61B 5/00* (2006.01)

(52) U.S. Cl.
CPC ........... *G05D 3/00* (2013.01); *A61B 2562/0295* (2013.01); *A61B 2560/0431* (2013.01); *A61B 5/145* (2013.01); *A61B 5/053* (2013.01); *A61B 5/6887* (2013.01); *A61B 5/7289* (2013.01)
USPC ............................. 700/214; 700/213; 700/244

(58) Field of Classification Search
None
See application file for complete search history.

(56) References Cited

U.S. PATENT DOCUMENTS

| | | | | |
|---|---|---|---|---|
| 3,993,452 A | * | 11/1976 | Moulding | ........................ 346/80 |
| 2012/0123233 A1 | * | 5/2012 | Cohen | ........................... 600/345 |

* cited by examiner

*Primary Examiner* — Yolanda Cumbess
(74) *Attorney, Agent, or Firm* — Ballard Spahr LLP

(57) ABSTRACT

A method of sampling includes receiving, by a portable bio-fluid sampling apparatus, a bio-fluid sample on a sample collection receptacle. The bio-fluid sample is associated with a timestamp that is indicative of a time at which the bio-fluid sample is received. The bio-fluid sample is stored in a bio-fluid chamber of the portable bio-fluid sampling apparatus.

20 Claims, 3 Drawing Sheets

METHOD AND SYSTEM FOR BIO-FLUID SAMPLING

CROSS-REFERENCE TO RELATED APPLICATIONS

This application claims the benefit of the filing date of U.S. Provisional Patent Application No. 61/551,001, filed Oct. 25, 2011, which is incorporated herein by reference in its entirety.

STATEMENT OF GOVERNMENT SUPPORT

This invention was made with United States government support under Grants 5000-59001975 and 5U10 HD 045986-05 awarded by the National Institutes of Health. The government has certain rights in this invention.

BACKGROUND

The following description is provided to assist the understanding of the reader. None of the information provided or references cited is admitted to be prior art.

Bio-fluids, which can include blood, saliva, urine, etc., are often sampled for the purpose of diagnosing a medical condition, testing for biomarkers, testing for presence or amount of a drug, etc. In most instances, samples of a bio-fluid are taken in a medical facility under the supervision of medical staff. For example, a nurse may draw blood using a syringe and provide the blood sample to a medical laboratory for analysis. Unfortunately, not all individuals have immediate access to medical facilities and medical staff. It can be difficult or impossible to diagnose, treat, or test such individuals using traditional sampling equipment and traditional sampling routines.

SUMMARY

An illustrative process of sampling includes receiving, by a portable bio-fluid sampling apparatus, a bio-fluid sample on a sample collection receptacle. The bio-fluid sample is associated with a timestamp that is indicative of a time at which the bio-fluid sample is received. The bio-fluid sample is stored in a bio-fluid chamber of the portable bio-fluid sampling apparatus.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
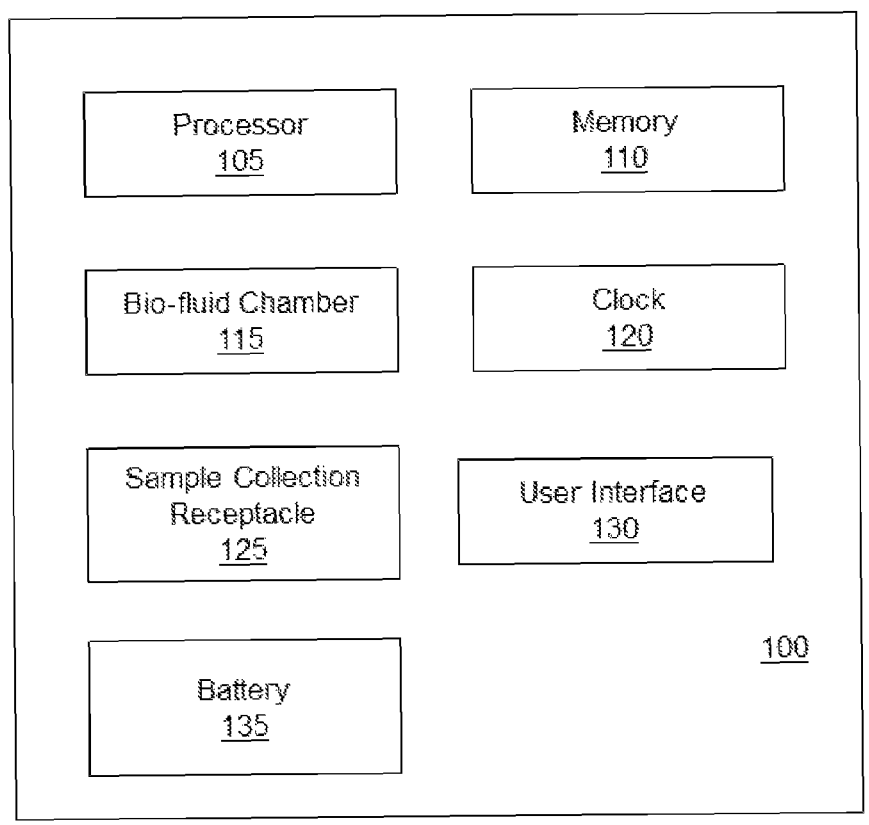
FIG. 1 is a block diagram illustrating a bio-fluid sampling apparatus in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a sample collection receptacle" can include two or more such sample collection receptacles unless the context indicates otherwise.

The word "or" as used herein means any one member of a particular list and also includes any combination of members of that list.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

FIG. 1 is a block diagram of a bio-fluid sampling apparatus 100 in accordance with an illustrative embodiment. Bio-fluid sampling apparatus 100 includes a processor 105, a memory 110, a bio-fluid chamber 115, a clock 120, a sample collection receptacle 125, a user interface 130, and a battery 135. In alternative embodiments, bio-fluid sampling apparatus 100 may include fewer, additional, and/or different components. In an illustrative embodiment, bio-fluid sampling apparatus 100 can be used to receive and store samples of a bio-fluid such as blood, saliva, urine, semen, etc. The bio-fluid can be from a human being or from a non-human subject, depending on the embodiment. In an illustrative embodiment, bio-fluid sampling apparatus can be fabricated from readily disposable components such that the production cost is low.

In one embodiment, a user places a bio-fluid sample onto or into sample collection receptacle 125. The user can be the individual whose sample is being taken. The user can also be a parent, relative, medical provider, etc. of the individual whose sample is being taken. In an illustrative embodiment, sample collection receptacle 125 can be a paper, cardboard, or filter paper card that is configured to absorb the bio-fluid sample. Alternatively, sample collection receptacle 125 can be a cup, a glass slide, or any other type of sample collection receptacle known to those of skill in the art. In an embodiment in which the bio-fluid sample is blood, the sample may be obtained by a pin prick to the finger of the individual providing the sample. Alternatively, the bio-fluid sample can be obtained by any other method known to those of skill in the art. The amount of bio-fluid that is collected in each sample can vary depending on the embodiment. In an illustrative embodiment, the bio-fluid sample has a small volume in the range of microliters (μL), such as, for example, a volume ranging from about 0.1 μL to about 75 μL and, more preferably, a volume ranging from about 10 μL to about 50 μL. Thus, it is contemplated that the volume of the bio-fluid sample can be about 0.1 μL, about 0.5 μL, about 1 μL, about 2 μL, about 5 μL, about 10 μL, about 50 μL, 75 μL, etc.). Such sample sizes are much smaller sample volumes as compared to samples obtained in conventional bio-fluid assay sampling.

For consistency, users can be instructed to place the same amount of bio-fluid on or in sample collection receptacle 125 each time that a bio-fluid sample is taken. In one embodiment, users can be provided with a small funnel into which bio-fluid can be placed. The opening at the bottom of the funnel can be sized to control the size of drops of bio-fluid that exit the funnel. In one embodiment, the user can be instructed to place exactly 1 drop of bio-fluid from the funnel onto or into sample collection receptacle 125. Alternatively, each bio-fluid sample may be 2 drops, 3 drops, 5 drops, etc. In another alternative embodiment, a syringe or other measuring device may be used instead of a funnel to control sample size.

Figure 2:
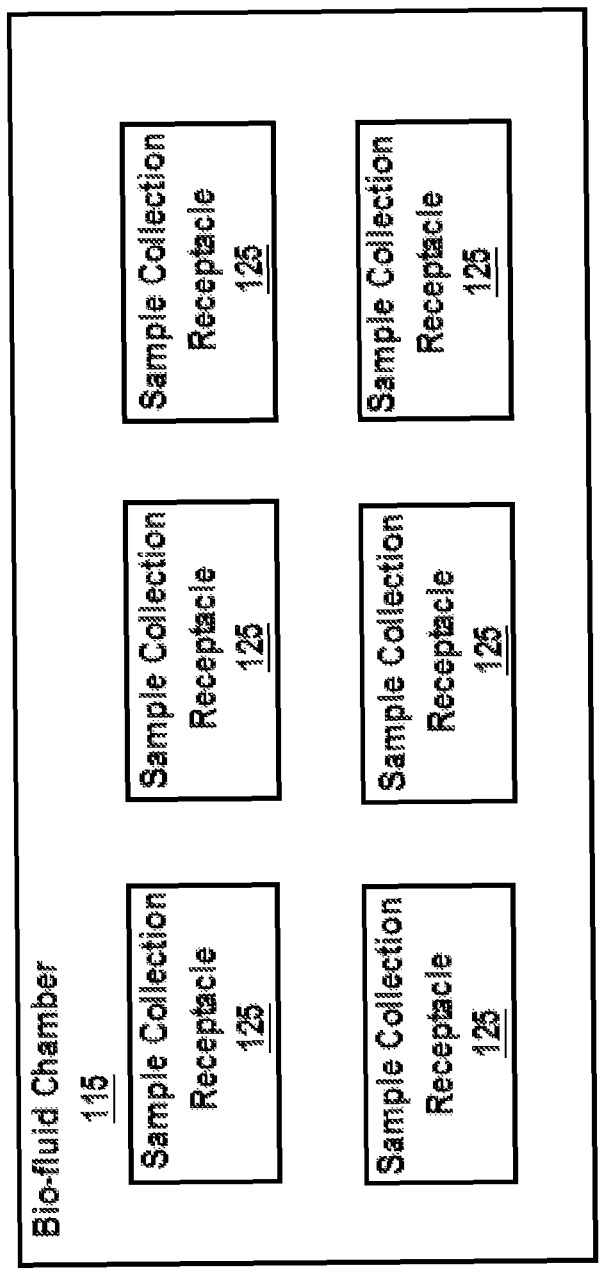
FIG. 2 is a schematic diagram depicting the positioning of sample collection receptacles within a bio-fluid chamber of the bio-fluid sampling apparatus of FIG. 1.

Once the bio-fluid sample is placed onto or into sample collection receptacle 125, the user can place sample collection receptacle 125 into bio-fluid chamber 115 of bio-fluid sampling apparatus 100. In one embodiment, bio-fluid chamber 115 can be a storage receptacle that is configured to receive and store a plurality of sample collection receptacles. A schematic diagram depicting the placement of a plurality of sample collection receptacles 125 into the bio-fluid chamber is provided in FIG. 2. In an illustrative embodiment, bio-fluid chamber 115 can hold up to six different samples on six different sample collection receptacles. In alternative embodiments, bio-fluid chamber may be configured to hold up to 1 sample, up to 3 samples, up to 10 samples, up to 25 samples, etc. As an example, bio-fluid chamber 115 can be in the form of a cassette that includes a plurality of slots/openings configured to receive a corresponding plurality of bio-fluid collection receptacles. The plurality of slots/openings can be separated by dividers such that the bio-fluid samples do not come into contact with one another while inside bio-fluid sampling apparatus. As such, bio-fluid sampling apparatus 100 can store samples collected over one or more days, one or more weeks, etc. In an alternative embodiment, other configurations of bio-fluid chamber 115 may be used. It is contemplated that the plurality of slots/openings can be oriented as required to facilitate analysis of the bio-fluid samples by conventional laboratory assay equipment.

Processor 105 can utilize clock 120 and/or memory 110 to associate a timestamp with each bio-fluid sample that is placed into bio-fluid sampling apparatus. The timestamp can include a time of day in hours, minutes, seconds, fractions of a second, etc. and/or a date that includes a month, day, and/or year. Processor 105 can be any type of computer processor known to those of skill in the art. In an illustrative embodiment, clock 120 can include an atomic style clock that is automatically synchronized with a remotely located atomic clock as known to those of skill in the art. Alternatively, clock 120 can be any other type of time keeping device or software known to those of skill in the art. Likewise, memory 110 can be any type of computer storage or computer memory known to those of skill in the art.

In one embodiment, processor 105 can use a printer or stamping device to print/stamp a timestamp on sample collection receptacle 125 when sample collection receptacle is placed into bio-fluid chamber 115. The timestamp can alternatively be imprinted onto sample collection receptacle 125. The timestamp can be printed, stamped, or imprinted on sample collection receptacle 125 when sample collection receptacle 125 is placed into bio-fluid chamber 115 or when sample collection receptacle 125 is removed from bio-fluid chamber 115, depending on the embodiment.

In an alternative embodiment, the timestamp can be stored in memory 110 and associated with a particular location of bio-fluid chamber 115. As an example, a first memory location can store a first timestamp associated with a bio-fluid sample that is placed into a first slot of bio-fluid chamber 115, a second memory location can store a second timestamp associated with a bio-fluid sample that is placed into a second slot of bio-fluid chamber 115, and so on. In such an embodiment, processor 105 can automatically detect when a bio-fluid sample is placed into a particular slot of bio-fluid chamber 115. Alternatively, the user can utilize user interface 130 to associate the timestamp with the proper slot of bio-fluid chamber 115. For example, the user may enter the timestamp information into user interface 130 such that the timestamp information is associated with a specific bio-fluid sample.

In another alternative embodiment, bio-fluid sampling apparatus 100 can be configured to automatically determine a timestamp for a bio-fluid sample when the bio-fluid sample is placed into bio-fluid sampling apparatus 100. As an example, if sample collection receptacle 125 is paper, cardboard, or filter paper, upon placement of sample collection receptacle 125 into bio-fluid chamber 115, bio-fluid sampling apparatus 100 can measure an impedance of one or more portions of the paper, cardboard, or filter paper that include the bio-fluid sample. The impedance can be measured using any method known to those of skill in the art. Based on the measured impedance, processor 105 can estimate a time at which the bio-fluid sample was placed onto sample collection receptacle 125. The time can be estimated using any methods known to those of skill in the art.

In one embodiment, processor 105 can be configured to print, stamp, imprint, etc. a bar code onto each sample collection receptacle 125. The bar code can include information that identifies the subject from which the bio-fluid sample was received. Such information can include the subject's name, insurance number, date of birth, social security number, address, telephone number, etc. In one embodiment, the bar code can also include the timestamp associated with the bio-fluid sample. In an alternative embodiment, the identifying information may be in any other form such as printed text, numerical code, watermark, etc. In another alternative embodiment in which the entire bio-fluid chamber 115 is sent to the laboratory for processing, the bar code may be placed onto bio-fluid chamber 115 and not on each individual sample collection receptacle 125. In another alternative embodiment, a portion or all of memory 110 may be incorporated within bio-fluid chamber 115 such that both memory 110 and bio-fluid chamber 115 are sent to the laboratory. In such an embodiment, the timestamp and/or bar code information may be incorporated into memory 110 for each of the bio-fluid samples included in bio-fluid chamber 115.

User interface 130 can be in the form of a keyboard, a touch screen, a mouse, and/or any other component known to those of skill in the art for allowing the user to interact with and control bio-fluid sampling apparatus 100. For example, a user can use user interface 130 to set clock 120. The user can also use user interface 130 to associate a timestamp with a given sample. User interface 130 may also be used to eject stored bio-fluid samples from bio-fluid sampling apparatus 100 so that the bio-fluid samples can be sent to a laboratory for processing.

Battery 135 can be any type of battery known to those of skill in the art, and can be used as a power source for bio-fluid sampling apparatus 100. As such, bio-fluid sampling apparatus 100 can be portable and be used by individuals that do not have access to a hospital or other medical facility. In an alternative embodiment, bio-fluid sampling apparatus 100 may include a power cord such that bio-fluid sampling apparatus 100 can receive power from an electrical outlet. The power cord can be in addition to battery 135 or can replace battery 135, depending on the embodiment.

In an illustrative embodiment, bio-fluid sampling apparatus 100 can be used by individuals in third world nations to store bio-fluid samples that can be sent to any laboratory around the world for testing and analysis. For example, it is very difficult for medical practitioners to monitor and test bio-fluids in children that live in third world nations. Using bio-fluid sampling apparatus 100, samples can be obtained from such children and sent to developed nations that have the laboratory equipment to test and analyze the samples. As such, medical providers are able to conduct clinical pharmacology studies in such children or other populations that are otherwise difficult to treat. The bio-fluid samples can be tested and/or analyzed to identify illness/disease, to identify concentrations of a drug for determining whether a proper dosage of the drug is being administered, to check for compliance with a drug/medicine regimen prescribed by a medical practitioner, for assay of drug or biomarker values, and/or for any other purpose known to those of skill in the art of laboratory analysis of bio-fluid samples. The laboratory that tests/analyzes the bio-fluid samples can use a standard tandem mass spectrometry device and/or any other devices known to those of skill in the art.

Any of the operations described herein can be performed by way of computer-readable instructions that are stored on a non-transitory computer-readable medium. In one embodiment, memory 110 can be a computer-readable medium that is configured to store such computer-readable instructions. Upon execution of the computer-readable instructions by processor 105, bio-fluid sampling apparatus 100 is caused to perform operations such as determining when a sample was taken, associating a timestamp with the sample, associating a bar code or other information with the sample, implementing instructions received through user interface 130, etc.

Figure 3:
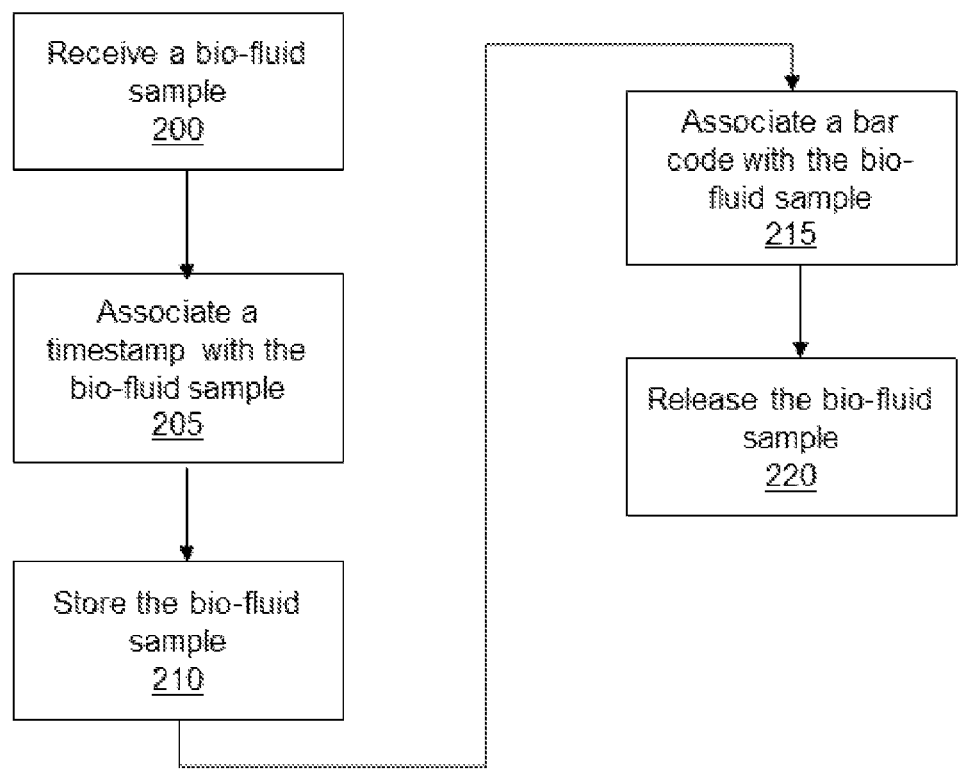
FIG. 3 is a flow diagram illustrating operations performed by a bio-fluid sampling apparatus in accordance with an illustrative embodiment.

FIG. 3 is a flow diagram illustrating operations performed by a bio-fluid sampling apparatus in accordance with an illustrative embodiment. In alternative embodiments, fewer, additional, and/or different operations may be performed. In addition, the use of a flow diagram is not meant to be limiting with respect to the order of operations performed. A bio-fluid sample is received in an operation 200. The bio-fluid sample can be received on or in a sample collection receptacle 125 as discussed above with reference to FIG. 1. In an illustrative embodiment, sample collection receptacle 125 is placed by the user into bio-fluid chamber 115. In an operation 205, a timestamp is associated with the bio-fluid sample. As described with reference to FIG. 1, the timestamp can be physically printed, stamped, or imprinted onto sample collection receptacle 125, or stored in memory 110. As also described above, the timestamp can be manually entered through user interface 130 by the user or automatically determined by bio-fluid sampling apparatus 100, depending on the embodiment.

In an operation 210, the bio-fluid sample is stored at the bio-fluid sampling apparatus. The bio-fluid sample can be stored in bio-fluid chamber 115 as described above. The bio-fluid sample can be stored for hours, days, weeks, etc. depending on the sample and its purpose. A bar code is associated with the bio-fluid sample in an operation 215. As described above, the bar code can include information identifying the subject that provided the sample and/or the timestamp information associated with the bio-fluid sample. Alternatively, a bar code may not be used and the information may be printed in text or conveyed in some other way. In an operation 220, the bio-fluid sample is released from the bio-fluid sampling apparatus. In one embodiment, the entire bio-fluid chamber 115 described above may be removed from bio-fluid sampling apparatus in the form of a cartridge or other device such that the cartridge or other device can be sent to a laboratory for analysis. In an alternative embodiment, the individual sample collection receptacles may be removed and provided individually to the laboratory.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention. It is intended that the scope of the invention be defined by the claims appended hereto and their equivalents.

What is claimed is:

1. A method of sampling comprising:
   receiving, by a portable bio-fluid sampling apparatus, a bio-fluid sample on a sample collection receptacle, the bio-fluid sample being provided by a subject, the sample collection receptacle being selected from the group consisting of paper, cardboard and filter paper;

associating, through a processor, the bio-fluid sample with a timestamp that is indicative of a time at which the bio-fluid sample is received, the processor being in operative communication with a clock;

associating, through a user interface, the bio-fluid sample with information about the subject; and analyzing the bio-fluid sample to determine at least one of a condition of the subject and a characteristic of the bio-fluid sample.

2. The method of claim 1, wherein the bio-fluid sampling apparatus comprises means for measuring the impedance for at least a portion of the sample collection receptacle containing the bio-fluid sample.

3. The method of claim 2, wherein the processor is configured to determine the timestamp for the bio-fluid sample based upon the measured impedance of the sample collection receptacle.

4. The method of claim 3, wherein the sample collection receptacle comprises filter paper.

5. The method of claim 1, wherein the bio-fluid sampling apparatus further comprises a memory in operative communication with the processor and the user interface, the memory being configured to store the timestamp associated with the bio-fluid sample and the information about the subject.

6. The method of claim 1, wherein the step of associating the bio-fluid sample with a timestamp comprises applying a bar code to the sample collection receptacle, the bar code being indicative of the timestamp associated with the bio-fluid sample.

7. The method of claim 1, wherein the method comprises analyzing the bio-fluid sample to determine a condition of the subject, and wherein the condition of the subject corresponds to an illness or disease.

8. The method of claim 1, wherein the method comprises analyzing the bio-fluid sample to determine a condition of the subject, and wherein the condition of the subject corresponds to a concentration of a drug.

9. The method of claim 8, wherein the concentration of the drug is used to determine whether a proper dosage of the drug is being administered to the subject in compliance with a prescribed drug regimen.

10. The method of claim 1, wherein the method comprises analyzing the bio-fluid sample to determine a characteristic of the bio-fluid sample, and wherein the characteristic of the bio-fluid sample corresponds to an assay of drug or biomarker values.

11. A method of sampling comprising:

sequentially receiving, by a portable bio-fluid sampling apparatus, a plurality of bio-fluid samples, the plurality of bio-fluid samples being provided by a subject;

associating, through a processor, each respective bio-fluid sample with a timestamp that is indicative of a time at which the bio-fluid sample is received, the processor being in operative communication with a clock, wherein the processor is configured to automatically detect when each respective bio-fluid sample is received by the portable bio-fluid sampling apparatus.

12. The method of claim 11, wherein the bio-fluid sampling apparatus comprises a memory in operative communication with the processor, the memory being configured to store the timestamp associated with each respective bio-fluid sample.

13. The method of claim 12, wherein the timestamp of each respective bio-fluid sample is associated with a particular location of the bio-fluid sampling apparatus.

14. The method of claim 11, wherein each bio-fluid sample is received by a sample collection receptacle.

15. The method of claim 14, wherein the bio-fluid sampling apparatus comprises means for measuring the impedance for at least a portion of the sample collection receptacle containing the bio-fluid sample.

16. The method of claim 15, wherein the processor is configured to determine the timestamp for each respective bio-fluid sample based upon the measured impedance of the sample collection receptacle.

17. The method of claim 14, wherein the sample collection receptacle is selected from the group consisting of paper, cardboard, and filter paper.

18. The method of claim 14, wherein the sample collection receptacle comprises filter paper.

19. A method of sampling comprising:

receiving, by a portable bio-fluid sampling apparatus, a bio-fluid sample on a sample collection receptacle;

associating the bio-fluid sample with a timestamp that is indicative of a time at which the bio-fluid sample is received; and storing the sample collection receptacle containing the bio-fluid sample in a bio-fluid chamber of the portable bio-fluid sampling apparatus, wherein the bio-fluid sampling apparatus comprises a processor and a clock, the processor being in operative communication with the clock, wherein the processor is configured to associate the bio-fluid sample with the timestamp, wherein the bio-fluid sampling apparatus comprises means for measuring the impedance for at least a portion of the sample collection receptacle containing the bio-fluid sample, and wherein the processor is configured to determine the timestamp for the bio-fluid sample based upon the measured impedance of the sample collection receptacle.

20. The method of claim 19, wherein the sample collection receptacle is selected from the group consisting of paper, cardboard, and filter paper.

* * * * *